United States Patent
Grammenos et al.

(10) Patent No.: US 6,469,195 B1
(45) Date of Patent: Oct. 22, 2002

(54) 2-PHENOXYPHENYLACETIC ACID DERIVATIVES, METHOD AND INTERMEDIATE PRODUCTS FOR THE PRODUCTION THEREOF, THEIR USE, AND AGENTS CONTAINING THE SAME FOR COMBATING FUNGICIDAL PESTS

(75) Inventors: Wassilios Grammenos, Ludwigshafen; Hubert Sauter, Mannheim; Andreas Gypser, Mannheim; Oliver Cullmann, Mannheim; Markus Gewehr, Kastellaun; Bernd Müller, Frankenthal; Arne Ptock, Ludwigshafen; Norbert Götz, Worms; Roland Götz, Neulussheim; Thorsten Volk, Mannheim; Eberhard Ammermann, Heppenheim; Thomas Grote, Schifferstadt; Gisela Lorenz, Neustadt; Siegfried Strathmann, Limburgerhof, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/830,365
(22) PCT Filed: Oct. 26, 1999
(86) PCT No.: PCT/EP99/08083
§ 371 (c)(1),
(2), (4) Date: Apr. 25, 2001
(87) PCT Pub. No.: WO00/26182
PCT Pub. Date: May 11, 2000

(30) Foreign Application Priority Data
Nov. 4, 1998 (DE) .......................... 198 50 729

(51) Int. Cl.⁷ .................. C07C 229/00; C07C 231/00
(52) U.S. Cl. ................... 560/35; 564/134; 564/147
(58) Field of Search .................. 560/35; 564/147

(56) References Cited

U.S. PATENT DOCUMENTS

| | | | |
|---|---|---|---|
| 4,829,085 A | 5/1989 | Wenderoth | 514/619 |
| 5,185,342 A * | 2/1993 | Hayase et al. | 514/724 |
| 5,395,854 A * | 3/1995 | Brand et al. | 514/619 |
| 5,412,149 A * | 5/1995 | Kuhnt et al. | 560/35 |

FOREIGN PATENT DOCUMENTS

| | | |
|---|---|---|
| EP | 253 213 | 1/1988 |
| EP | 254 426 | 1/1988 |
| EP | 398 692 | 11/1990 |
| EP | 477 631 | 4/1992 |
| GB | 2 249 092 | 4/1992 |

* cited by examiner

Primary Examiner—Paul J. Killos
(74) Attorney, Agent, or Firm—Keil & Weinkauf

(57) ABSTRACT

2-Phenoxyphenylacetic acid derivatives of the formula I

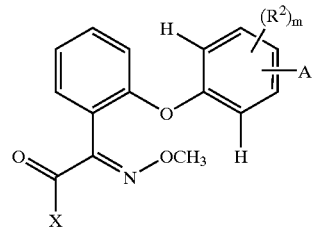

where the substituents and the index have the following meanings:

A is

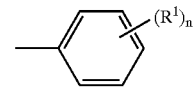

where $R_1$ is halogen, $C_1$–$C_4$-alkyl, $C_1$–$C_4$-alkoxy, $CF_3$, $C_1$–$C_4$-haloalkoxy, formyl, $C(=O)NR^aR^b$ or $C(R^a)=NOR^b$;
$R^a$ is hydrogen or $C_1$–$C_4$-alkyl;
$R^b$ is $C_1$–$C_4$-alkyl;
n is 1, 2, 3 or 4, where the groups $R^1$ may be different if n is not 1;
$R^2$ is halogen, $CH_3$ or $CF_3$;
m is 0 or 1; and
X is $OCH_3$ or $NHCH_3$;

processes and intermediates for preparing the compounds I and the use of the compounds I for controlling harmful fungi are described.

9 Claims, No Drawings

2-PHENOXYPHENYLACETIC ACID DERIVATIVES, METHOD AND INTERMEDIATE PRODUCTS FOR THE PRODUCTION THEREOF, THEIR USE, AND AGENTS CONTAINING THE SAME FOR COMBATING FUNGICIDAL PESTS

TECHNICAL FIELD

The present invention relates to 2-phenoxyphenylacetic acid derivatives of the formula I:

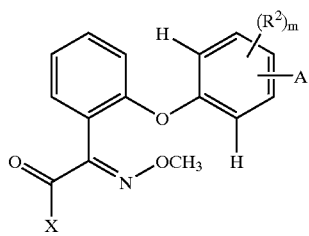

where the substituents and the index have the following meanings:

A is

where $R^1$ is halogen, $C_1-C_4$-alkyl, $C_1-C_4$-alkoxy, $CF_3$, $C_1-C_4$-haloalkoxy, formyl, $C(=O)NR^aR^b$ or $C(R^a)=NOR^b$;
$R^a$ is hydrogen or $C_1-C_4$-alkyl;
$R^b$ is $C_1-C_4$-alkyl;
n is 1, 2, 3 or 4, where the groups $R^1$ may be different if n is not 1;
$R^2$ is halogen, $CH_3$ or $CF_3$;
m is 0 or 1; and
X is $OCH_3$ or $NHCH_3$.

In addition, the invention relates to processes and intermediates for preparing the compounds I, and to the use of the compounds I for controlling harmful fungi.

BACKGROUND ART

2-Phenoxyphenylacetic esters are known from EP-A 253 213 and EP-A 254 426, and the corresponding amides are described in 45 EP-A 398 692 and EP-A 477 631. The compounds described in the abovementioned publications are suitable for use as crop protection agents against harmful fungi.

However, in many instances their activity is unsatisfactory.

DISCLOSURE OF INVENTION

It is an object of the present invention to provide compounds having improved activity.

We have found that this object is achieved by the 2-phenoxyphenylacetic acid derivatives of the formula I. Furthermore, we have found intermediates and processes for preparing the compounds I, and their use, and compositions comprising them for controlling harmful fungi.

The compounds of the formula I differ from the compounds known from the abovementioned publications in the specific variation of the substitution at the 2-phenoxy radical by a substituted phenyl ring in meta- or para-position and, if appropriate, a further substituent in meta- or para-position.

The compounds of the formula I can be obtained per se by the processes described in EP-A 253 213, EP-A 254 426, EP-A 398 692 and EP-A 477 631.

MODE(S) FOR CARRYING OUT THE INVENTION

In particular, the compounds of the formula I are obtained by reacting alkyl α-phenyl-α-ketoacetates of the formula II under basic conditions with phenols of the formula III to give alkyl α-(2-phenoxyphenyl)-α-ketoacetates of the formula IV. In formula II, L is a leaving group customary for nucleophilic aromatic substitution, such as halogen, in particular fluorine or chlorine, or sulfonate or nitro. This reaction is carried out under generally customary conditions, similar to WO-A 97/24317.

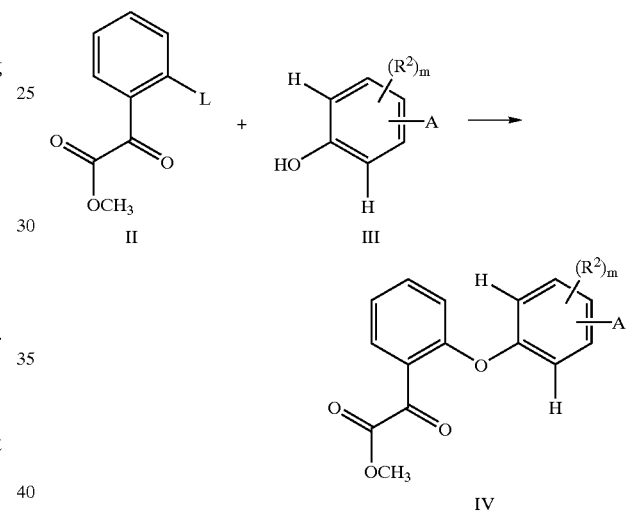

Keto esters IV are reacted with O-methylhydroxylamine or its acid addition salt of the formula Va, if appropriate in the presence of a base, under the conditions described in EP-A 493 711, to give oxime ethers of the formula IA.

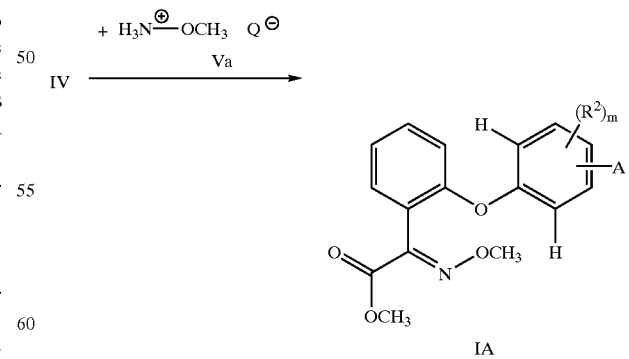

If X in the formula I is $NHCH_3$, the esters of the formula IA are converted with methylamine according to methods known from EP-A 398 692 into the amides of the formula IB.

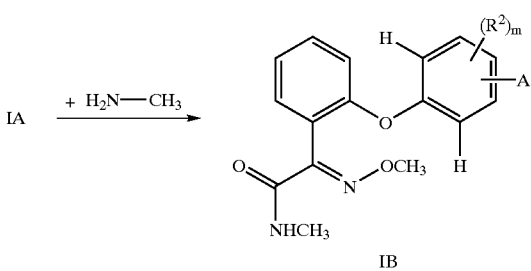

In the formula Va, Q is the anion of an inorganic acid, in particular a halide ion.

Phenols of the formula III are known from the literature, or they can be obtained by methods known from the literature [cf.: WO-A 96/23749; WO-A 97/18188; JP-A 04/173756; JP-A 08/157406; EP-A 625 726; Synthesis (1990), 827–833].

Alternatively, the compounds of the formula I can also be obtained by the method known from WO-A 95/34526.

In a further process, compounds of the formula I can also be prepared from compounds of the formula VI by transition-metal-catalyzed coupling with a phenyl derivative of the formula VII.

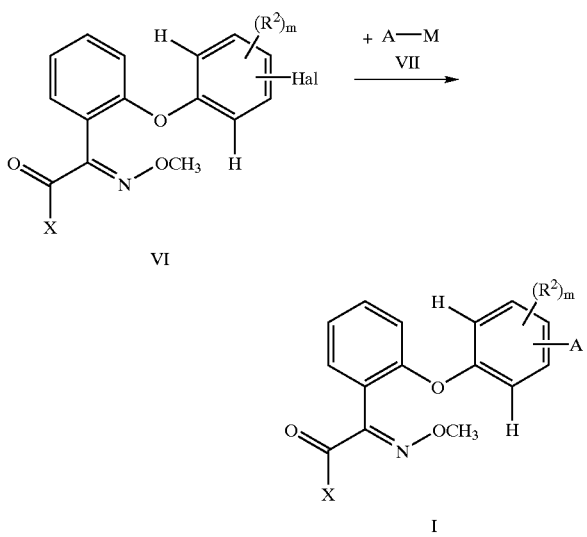

In formula VII, M is an organometallic radical, such as, for example, $B(OH)_2$, $Sn(CH_3)_3$, $Sn(n-C_4H_9)_3$, Mg—Hal or Zn—Hal. In formulae VI and VII, "Hal" is a halogen atom, such as chlorine, bromine or iodine, in particular bromine and iodine.

The reaction of VI with VII is generally carried out at 10° C.–150° C., preferably at 50° C.–120° C., in an inert organic solvent [cf. WO-A 98/11070; Synth. Commun. (1981), 513; Angew. Chem. Ind. Ed. (1986), 508]. If M in the formula VII is $B(OH)_2$, the reaction is carried out in the presence of a base [cf. Synth. Commun. (1981), 513; ibid (1994), 709; J. Het. Chem. (1989), 865; J. Org. Chem. (1988), 2052; ibid (1994), 6095].

Suitable solvents are ethers, such as dioxane, dimethoxyethane and tetrahydrofuran. It is also possible to use mixtures of the abovementioned solvents.

Bases which are suitable for the Suzuki reaction are, for example, potassium carbonate, sodium carbonate, sodium bicarbonate and triethylamine.

Suitable catalysts are, for example: trans-bis(acetonitrile)palladium(II) chloride, bis(dibenzylideneacetone)palladium (0), bis(triphenylphosphine)palladium(II) chloride, palladium acetate, palladium chloride and tetrakis(triphenylphosphine)palladium(0).

The compounds of the formula VI are known from EP-A 253 213, EP-A 254 426, EP-A 398 692 and EP-A 477 631, or they can be obtained by the routes described in these publications.

If individual compounds I are not obtainable by the routes described above, they can be prepared by derivatization of other compounds I.

The reaction mixtures are worked up in a customary manner, for example by mixing with water, phase separation and, if required, chromatographic purification of the crude products. Some of the intermediates and end products are obtained in the form of colorless or slightly brownish, viscous oils, which are purified or freed from volatile components under reduced pressure and at moderately elevated temperature. If the intermediates and end products are obtained as solids, purification can also be carried out by recrystallization or digestion.

Owing to their C=N double bonds, the preparation of the compounds I may yield E/Z isomer mixtures which can be separated into the individual compounds in a customary manner, for example by crystallization or chromatography.

However, if the synthesis yields isomer mixtures, a separation is generally not necessarily required since in some cases the individual isomers can be converted into one another during the preparation for use or upon use (for example under the action of light, acids or bases). Similar conversions may also occur after use, for example in the treatment of plants in the treated plant or in the harmful fungus to be controlled.

With regard to the C=NOCH$_3$ double bond, preference, on account of their activity, is given to the E isomers of the compounds I (configuration based on the OCH$_3$ group in relation to the COX group).

In the symbol definitions given in the formulae above, collective terms were used which generally represent the following substituents:

Halogen: fluorine, chlorine, bromine and iodine;

Alkyl: saturated, straight-chain or branched hydrocarbon radicals having 1 to 4 carbon atoms, for example $C_1$–$C_4$-alkyl, such as methyl, ethyl, propyl, 1-methylethyl, butyl, 1-methylpropyl, 2-methylpropyl and 1,1-dimethylethyl;

Haloalkyl: straight-chain or branched alkyl groups having 1 to 4 carbon atoms (as mentioned above), where in these groups some or all of the hydrogen atoms may be replaced by halogen atoms as mentioned above, for example $C_1$–$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Alkoxy: straight-chain or branched alkyl groups having 1 to 4 carbon atoms (as mentioned above) which are attached to the skeleton via an oxygen atom (—O—);

Haloalkoxy: straight-chain or branched haloalkyl groups having 1 to 4 carbon atoms (as mentioned above) which are attached to the skeleton via an oxygen atom (—O—);

Alkylamino: a straight-chain or branched alkyl group having 1 to 4 carbon atoms (as mentioned above) which is attached to the skeleton via an amino group (—NH—);

Dialkylamino: two straight-chain or branched alkyl groups which are independent of one another and in each case have 1 to 4 carbon atoms (as mentioned above) which are attached to the skeleton via a nitrogen atom;

Alkoxycarbonyl: an alkoxy group having 1 to 4 carbon atoms (as mentioned above) which is attached to the skeleton via a carbonyl group (—CO—);

Alkylaminocarbonyl: an alkylamino group having 1 to 4 carbon atoms (as mentioned above) which is attached to the skeleton via a carbonyl group (—CO—);

Dialkylaminocarbonyl: a dialkylamino group (as mentioned above) which is attached to the skeleton via a carbonyl group (—CO—).

With regard to the intended use of the 2-phenoxyphenylacetic acid derivatives of the formula I, particular preference is given to the following meanings of the substituents, in each case on their own or in combination:

Particular preference is given to compounds IB.

Moreover, particular preference is given to compounds I in which the index m is zero.

Likewise, particular preference is given to compounds I in which the index n is 1 or 2.

In addition, particular preference is given to compounds I in which the group A is in position 3.

Particular preference is also given to compounds I in which $R^1$ is halogen, $C_1$–$C_4$-alkoxy, $CF_3$, $C_1$–$C_4$-haloalkoxy, $C_1$–$C_4$-alkoxycarbonyl, $C_1$–$C_4$-alkylaminocarbonyl or di-($C_1$–$C_4$-alkyl)aminocarbonyl.

Particular preference is also given to compounds I in which $R^1$ is fluorine, chlorine or $CF_3$.

Furthermore, preference is also given to compounds I in which $R^1$ is in position 4.

In addition, preference is also given to compounds I in which two groups $R^1$ are in the 2,4-position.

The particularly preferred embodiments of the intermediates of the formula IV with regard to the variables correspond to those of the radicals $R^1$, $R^2$ and A of the formula I.

The compounds I are suitable as fungicides. They have excellent activity against a broad spectrum of phytopathogenic fungi, in particular from the class of the Ascomycetes, Deuteromycetes, Phycomycetes and Basidiomycetes. Some of them act systemically and can be employed in crop protection as foliar- and soil-acting fungicides.

They are especially important for controlling a large number of fungi in a variety of crop plants such as wheat, rye, barley, oats, rice, maize, grass, bananas, cotton, soya, coffee, sugar cane, grape vines, fruit species, ornamentals and vegetable species such as cucumbers, beans, tomatoes, potatoes and cucurbits, and also in the seeds of these plants.

Specifically, they are suitable for controlling the following plant diseases:

Alternaria species in vegetables and fruit,

*Botrytis cinerea* (gray mold) in strawberries, vegetables, ornamentals and grape vines,

*Cercospora arachidicola* in groundnuts,

*Erysiphe cichoracearum* and *Sphaerotheca fuliginea* in cucurbits,

*Erysiphe graminis* (powdery mildew) in cereals,

Fusarium and Verticillium species in a variety of plants,

Helminthosporium species in cereals,

Mycosphaerella species in bananas and groundnuts,

*Phytophthora infestans* in potatoes and tomatoes,

*Plasmopara viticola* in grape vines,

*Podosphaera leucotricha* in apples,

*Pseudocercosporella herpotrichoides* in wheat and barley,

Pseudoperonospora species in hops and cucumbers,

Puccinia species in cereals,

*Pyricularia oryzae* in rice,

Rhizoctonia species in cotton, rice and lawns,

*Septoria nodorum* in wheat,

*Uncinula necator* in grape vines,

Ustilago species in cereals and sugar cane, and

Venturia species (scab) in apples and pears.

The compounds I are also suitable for controlling harmful fungi such as *Paecilomyces variotii* in the protection of materials (for example wood, paper, paint dispersions, fibers or fabrics) and in the protection of stored products.

The compounds I are employed by treating the fungi or the plants, seeds, materials or the soil to be protected against fungal attack with a fungicidally effective amount of the active compounds. The application may be carried out before or after the infection of the materials, plants or seeds by the fungi.

The fungicidal compositions generally comprise from 0.1 to 95, preferably from 0.5 to 90%, by weight of active compound.

For use in crop protection, the application rates are, depending on the kind of effect desired, from 0.01 to 2.0 kg of active compound per ha.

The treatment of seeds generally requires active compound quantities of from 0.001 to 0.1 g, preferably from 0.01 to 0.05 g, per kilogram of seed.

For use in the protection of materials or stored products, the active compound application rate depends on the kind of application area and effect desired. Customary application rates in the protection of materials are, for example, from 0.001 g to 2 kg, preferably from 0.005 g to 1 kg, of active compound per cubic meter of treated material.

The compounds I can be converted into the customary formulations, e.g. solutions, emulsions, suspensions, dusts, powders, pastes and granules. The use form depends on the specific intended use; in any case, it should ensure fine and uniform distribution of the compound according to the invention.

The formulations are prepared in a known manner, e.g. by extending the active compound with solvents and/or carriers, if desired using emulsifiers and dispersants, it also being possible to use other organic solvents as auxiliary solvents if water is used as the diluent. Suitable auxiliaries for this purpose are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water; carriers such as ground natural minerals (e.g. kaolins, clays, talc, chalk) and ground synthetic minerals (e.g. finely divided silica, silicates); emulsifiers such as nonionic and anionic emulsifiers (e.g. polyoxyethylene fatty alcohol ethers, alkylsulfonates and arylsulfonates), and dispersants such as ligninsulfite waste liquors and methylcellulose.

Suitable surfactants are the alkali metal, alkaline earth metal and ammonium salts of lignosulfonic acid, naphthalenesulfonic acid, phenolsulfonic acid and dibutylnaphthalenesulfonic acid, alkylarylsulfonates, alkyl sulfates, alkylsulfonates, fatty alcohol sulfates and fatty acids and alkali metal salts and alkaline earth metal salts thereof, salts of sulfated fatty alcohol glycol ethers, condensation products of sulfonated naphthalene and naphthalene derivatives with formaldehyde, condensation products of naphthalene or of naphthalene sulfonic acid with phenol and formaldehyde, polyoxyethylene octylphenol ethers, ethoxylated isooctylphenol, octylphenol and nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Suitable for preparing directly sprayable solutions, emulsions, pastes or oil dispersions are petroleum fractions having medium to high boiling points, such as kerosine or diesel fuel, furthermore coal-tar oils and oils of plant or animal origin, aliphatic, cyclic and aromatic hydrocarbons, for example benzene, toluene, xylene, paraffin, tetrahydronaphthalene, alkylated naphthalenes or derivatives thereof, methanol, ethanol, propanol, butanol, chloroform, carbon tetrachloride, cyclohexanol, cyclohexanone, chlorobenzene, isophorone, strongly polar solvents, for example dimethylformamide, dimethyl sulfoxide, N-methylpyrrolidone, and water.

Powders, compositions for broadcasting and dusts can be prepared by mixing or jointly grinding the active substances with a solid carrier.

Granules, for example coated granules, impregnated granules and homogeneous granules, can be prepared by binding the active compounds to solid carriers. Solid carriers are, for example, mineral earths, such as silica gel, silicas, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as ammonium sulfate, ammonium phosphate, ammonium nitrate, ureas and products of vegetable origin, such as cereal meal, tree bark meal, wood meal and nutshell meal, cellulose powders and other solid carriers.

The formulations generally comprise from 0.01 to 95% by weight, preferably from 0.1 to 90% by weight, of the active compound. The active compounds are employed in a purity of from 90% to 100%, preferably from 95% to 100% (according to the NMR spectrum).

Examples of formulations are:

I. 5 parts by weight of a compound according to the invention are thoroughly mixed with 95 parts by weight of finely divided kaolin. This affords a dusting composition comprising 5% by weight of the active compound.

II. 30 parts by weight of a compound according to the invention are thoroughly mixed with a mixture of 92 parts by weight of pulverulent silica gel and 8 parts by weight of paraffin oil which had been sprayed onto the surface of this silica gel. This affords an active compound preparation having good adhesive properties (active compound content 23% by weight).

III. 10 parts by weight of a compound according to the invention are dissolved in a mixture comprising 90 parts by weight of xylene, 6 parts by weight of the addition product of 8 to 10 mol of ethylene oxide to 1 mol of oleic acid N-monoethanolamide, 2 parts by weight of the calcium salt of dodecylbenzenesulfonic acid and 2 parts by weight of the addition product of 40 mol of ethylene oxide to 1 mol of castor oil (active compound content 9% by weight).

IV. 20 parts by weight of a compound according to the invention are dissolved in a mixture comprising 60 parts by weight of cyclohexanone, 30 parts by weight of isobutanol, 5 parts by weight of the addition product of 7 mol of ethylene oxide to 1 mol of isooctylphenol and 5 parts by weight of the addition product of 40 mol of ethylene oxide to 1 mol of castor oil (active compound content 16% by weight).

V. 80 parts by weight of a compound according to the invention are mixed well with 3 parts by weight of the sodium salt of diisobutylnaphthalene-alpha-sulfonic acid, 10 parts by weight of the sodium salt of a lignosulfonic acid from a sulfite waste liquor and 7 parts by weight of pulverulent silica gel, and ground in a hammer mill (active compound content 80% by weight).

VI. 90 parts by weight of a compound according to the invention are mixed with 10 parts by weight of N-methyl-α-pyrrolidone, affording a solution which is suitable for use in the form of very small drops (active compound content 90% by weight).

VII. 20 parts by weight of a compound according to the invention are dissolved in a mixture comprising 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. The solution is poured into 100,000 parts by weight of water and finely dispersed therein, affording an aqueous dispersion comprising 0.02% by weight of the active compound.

VIII. 20 parts by weight of a compound according to the invention are mixed well with 3 parts by weight of the sodium salt of diisobutylnaphthalene-α-sulfonic acid, 17 parts by weight of the sodium salt of a lignosulfonic acid from a sulfite waste liquor and 60 parts by weight of pulverulent silica gel, and ground in a hammer mill. The mixture is finely dispersed in 20,000 parts by weight of water, affording a spray liquor comprising 0.1% by weight of the active compound.

The active compounds can be applied as such, in the form of their formulations or in the application forms prepared therefrom, for example in the form of directly sprayable solutions, powders, suspensions or dispersions, emulsions, oil dispersions, pastes, dusts, compositions for broadcasting, or granules, by spraying, atomizing, dusting, broadcasting or watering. The application forms depend entirely on the intended uses; in any case, they should ensure very fine dispersion of the active compounds according to the invention.

Aqueous use forms can be prepared from emulsion concentrates, pastes or wettable powders (spray powders, oil dispersions) by addition of water. To prepare emulsions, pastes or oil dispersions, the substances can be homogenized in water as such or dissolved in an oil or solvent, by means of wetting agents, tackifiers, dispersants or emulsifiers. However, concentrates comprising active substance, wetting agent, tackifier, dispersant or emulsifier and possibly solvent or oil which are suitable for dilution with water can also be prepared.

The active compound concentrations in the ready-to-use preparations can be varied over a relatively wide range. In general, they are from 0.0001 to 10%, preferably from 0.01 to 1%.

It is also possible to use the active compounds with good success in the ultra-low-volume method (ULV), it being possible to apply formulations comprising more than 95% by weight of active compound or even the active compound without additives.

Oils of various types, herbicides, fungicides, other pesticides and bactericides can be added to the active compounds, if desired even immediately prior to application (tank mix). These agents can be added to the compositions according to the invention in a weight ratio of 1:10 to 10:1.

The compositions according to the invention in the use form as fungicides may also be present in combination with other active compounds, for example with herbicides, insecticides, growth regulators, fungicides or else with fertilizers. In many cases, a mixture of the compounds I, or of the compositions comprising them, in the use form as fungicides with other fungicides results in a broader fungicidal spectrum of activity.

The following list of fungicides in combination with which the compounds according to the invention can be used is intended to illustrate the possible combinations, but not to impose any limitation:

sulfur, dithiocarbamates and their derivatives, such as iron (III) dimethyldithiocarbamate, zinc dimethyldithiocarb-amate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis(thiocarbamoyl)disulfide;

nitro derivatives, such as dinitro-(1-methylheptyl)phenyl crotonate, 2-sec-butyl-4,6-dinitrophenyl-3,3-dimethyl acrylate, 2-sec-butyl-4,6-dinitrophenylisopropyl carbonate, diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(furyl-(2)) benzimidazole, 2-(thiazolyl-(4))benzimidazole, N-(1,1,2,2-tetrachloroethylthio)tetrahydrophthalimide, N-trichloromethylthiotetrahydrophthalimide. N-trichloromethylthiophthalimide, N-dichlorofluoromethylthio-N',N'-dimethyl-N-phenylsulfuric diamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine 2-thio-1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine-4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine 2,2,2-trichloroethyl acetal, piperazine-1,4-diyl-bis-1-(2,2,2-trichloroethyl) formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolyl-urea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS, 3RS)-1-[3-(2-chlorophenyl)-2-(4-fluorophenyl)-oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis-(3-methoxycarbonyl-2-thioureido)benzene, strobilurins, such as methyl E-methoxyimino-[α-(o-tolyloxy)-o-tolyl]acetate, methyl E-2-{2-[6-(2-cyanophenoxy)-pyridimin-4-yloxy]-phenyl}-3-methoxy acrylate, N-methyl E-methoxyimino-[α-(2-phenoxyphenyl)]acetamide, methyl-E-methoxyimino-[α-(2,5-dimethylphenoxy)-o-tolyl]acetamide, anilinopyrimidines, such as N-(4,6-dimethylpyrimidin-2-yl)aniline, N-[4-methyl-6-(1-propynyl)pyrimidin-2-yl]aniline, N-(4-methyl-6-cyclopropylpyrimidin-2-yl)aniline, phenylpyrroles, such as 4-(2,2-difluoro-1,3-benzodioxol-4-yl)pyrrole-3-carbonitrile, cinnamides, such as 3-(4-chlorophenyl)-3-(3,4-dimethoxyphenyl)acryloylmorpholine;

and a variety of fungicides, such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)-N-(2-furoyl)-DL-alaninate, DL-N-(2,6-dimethylphenyl)-N-(2'-methoxyacetyl) alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropyl carbamoylhydantoin, N-(3,5-dichlorophenyl)-1,2-dimethylcyclopropane-1,2-dicarboximide, 2-cyano-[N-(ethylaminocarbonyl)-2-methoximino]acetamide, 1-[2-(2,4-dichlorophenyl) pentyl]-1H-1,2,4-triazole, 2,4-difluoro-a-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis-(4-fluorophenyl) methylsilyl)methyl-1H-1,2,4-triazole

SYNTHESIS EXAMPLES

The procedures given in the synthesis examples below were used to obtain further compounds I by appropriate modification of the starting materials. The compounds obtained in this manner are listed in the tables which follow, together with physical data.

Example 1

Preparation of Methyl [2-(3-Bromo-4-fluorophenoxy)phenyl]oxoacetate

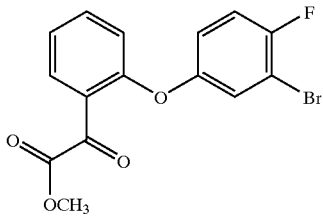

A suspension of 3.75 g of 80% pure NaH in 50 ml of dimethyl sulfoxide (DMSO) was admixed with 21.7 g of 3-bromo-4-fluorophenol (cf. DE-A 192 80 27) and then stirred at 20–25° C. for 30 min, and a solution of 22.7 g of methyl 2-(2-fluorophenyl)oxoacetate in 100 ml of DMSO was added dropwise. The reaction mixture was stirred at 20–25° C. for approximately 12 hours, poured into ice-water and then extracted with ethyl acetate. The organic phases were washed with 1 N aqueous sodium hydroxide solution and water and dried, and the solvent was distilled off, giving 35 g of the title compound.

$^1$H NMR (CDCl$_3$, ppm): δ=3.7 (3H); 6.7–8.0 (7H).

Example 2

Preparation of Methyl E-[2-(3-Bromo-4-fluorophenoxy)phenyl]methoxyiminoacetate

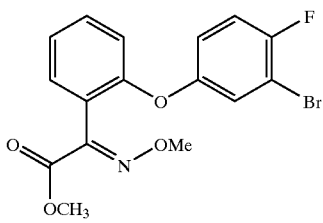

A solution of 10.3 g of the keto ester from Example 1 in 100 ml of methanol was admixed with 3.7 g of O-methoxyamine hydrochloride and stirred at 20–25° C. for 30 hours. The solvent was removed and the residue was then taken up in ethyl acetate, washed with water and then dried. The solvent was distilled off and the residue was chromatographed over silica gel (methyl tert-butyl ether [MtBE]/cyclohexane=9:1), giving 4.4 g of the title compound and 1.9 g of the Z-isomer.

$^1$H NMR (CDCl$_3$, ppm): δ=3.8 (3H); 4.0 (3H); 6.8–7.5 (7H).

Example 3

Preparation of 2-[2-(3-Bromo-4-fluorophenoxy)phenyl]-2-methoxyimino-N-methylacetamide

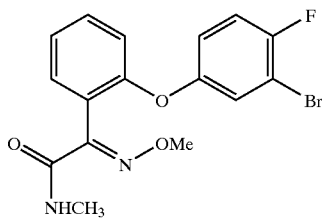

The solution of 4.4 g of the E-isomer from Example 3 in 80 ml of tetrahydrofuran was admixed with 8 g of 40% strength aqueous methylamine solution and stirred at 20–25° C. for 3 hours. The mixture was then poured into water and extracted with ethyl acetate, and the ethyl acetate phases were washed with water and then dried. Distillative removal of the solvent and silica gel chromatography (MtBE:cyclohexane=9:1) gave 3.9 g of the title compound.

$^1$H NMR (CDCl$_3$, ppm): δ=2.9 (3H); 3.9 (3H); 6.7 (1H); 6.9–7.5 (7H).

Example 4

Preparation of 2-[2-(6-Fluoro-4'-methylbiphenyl-3-yloxy) phenyl]-2-methoxyimino-N-methylacetamide

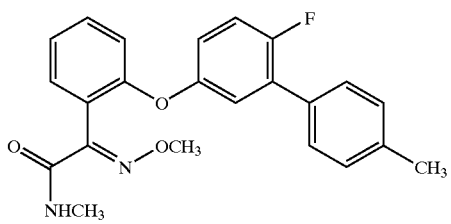

A solution of 0.3 g of the product from Example 3 in 15 ml of dimethoxyethane was admixed with 0.2 g of 4-methylphenylboronic acid, 0.17 g of sodium carbonate, 2 ml of water and 40 mg of tetrakis(triphenylphosphine)palladium(0) and refluxed for 20 hours. The mixture was then poured into water and extracted with ethyl acetate, and the extract was washed with 1N aqueous sodium hydroxide solution and then with water and dried. Distillative removal of the solvent and silica gel chromatography (MtBE:cyclohexane=9:1) gave 0.3 g of the title compound.

$^1$H NMR (CDCl$_3$, ppm): δ=2.38 (3H); 2.9 (3H); 4.0 (3H); 6.8 (1H) 6.9–7.5 (11H)

Example 5

Preparation of Methyl E/Z-[2-(3-Iodophenoxy)phenyl]-methoxyiminoacetate

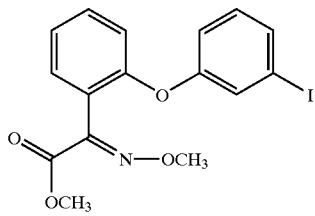

55 g of 3-iodophenol were added dropwise to a suspension of 6.9 g of 95% pure NaH in 50 ml of dimethyl sulfoxide (DMSO). The mixture was stirred at 25–33° C. for 30 min, after which a solution of 44.5 g of methyl 2-(2-fluorophenyl)oxoacetate in 80 ml of DMSO was added dropwise. The reaction mixture was stirred at 20–25° C. for approximately 48 hours and then poured into ice-water and extracted with methyl tert-butyl ether (MtBE). The organic phases were washed with 1N aqueous sodium hydroxide solution and water and dried and then freed from the solvent. The residue was taken up in 1 liter of methanol and admixed with 143 ml of a 17.5% strength aqueous methoxyamine solution. The mixture was stirred at 20–25° C. for 12 hours, after which the methanol was distilled off, the residue was taken up in MtBE and water and the organic phases were dried. Removal of the solvent gave 58 g of the title compound as an E/Z-isomer mixture which was used without any further purification in Example 6.

Example 6

Preparation of Methyl E-[2-(3-Iodophenoxy)phenyl]-methoxyiminoacetate

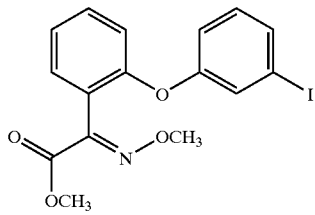

With ice-cooling, a solution of 75 g of the isomer mixture from Example 5 in 350 ml of ethanol was saturated with hydrogen chloride and stirred at 20–25° C. for 12 hours. Distillative removal of the solvent and silica gel chromatography (MtBE/cyclohexane=9:1) gave 48 g of pure E-isomer as a yellow oil.

$^1$H NMR (CDCl$_3$, ppm): δ=3.82 (3H); 4.0 (3H); 6.9–7.5 (8H).

Example 7

Preparation of 2-[2-(3-Iodophenoxy)-phenyl]-2-methoxyimino-N-methylacetamide

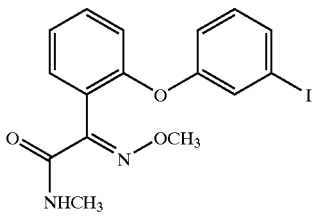

A solution of 47 g of E-isomer from Example 6 in 180 ml of tetrahydrofuran was admixed with 80 g of 40% strength aqueous methylamine solution and stirred at 20–25° C. for 2 hours. The mixture was then poured into water and extracted with ethyl acetate, and the ethyl acetate phases were washed with water and then dried. Distillative removal of the solvent and silica gel chromatography (MtBE:cyclohexane=9:1) gave 42.4 g of the title compound as a yellow oil.

$^1$H NMR (CDCl$_3$, ppm): δ=2.9 (3H); 3.9 (3H); 6.7 (1H); 6.9–7.4 (8H).

Example 8

Preparation of 2-[2-(4'-Chlorobiphenyl-3-yloxy)phenyl]-2-methoxyimino-N-methylacetamide

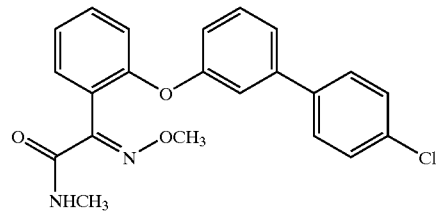

A solution of 13 g of the product from Example 7 in 105 ml of dimethoxyethane was admixed with 9.9 g of 4-chlorophenylboronic acid, 6.7 g of sodium carbonate, 34 ml of water and 200 mg of tetrakis(triphenylphosphine)palladium(0) and refluxed for 3 hours. The mixture was then poured into water and extracted with ethyl acetate, and the extract was washed with 1N aqueous sodium hydroxide solution and then with water and dried. Distillative removal of the solvent and silica gel chromatography (MtBE:cyclohexane=9:1) gave 9.5 g of product as colorless crystals of m.p. 118–121° C.

$^1$H NMR (CDCl$_3$, ppm): δ=2.9 (3H); 4.0 (3H); 6.7 (1H); 6.9–7.5 (12H).

Example 9

Preparation of Methyl E/Z-[2-(4'-Chlorobiphenyl-3-yl-oxy)phenyl]methoxyiminoacetate

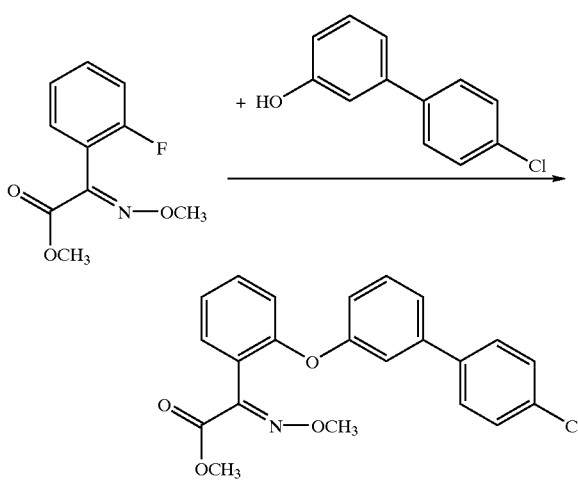

A solution of 5 g of 4'-chlorobiphenyl-3-ol (cf. WO 96/23749) in 40 ml of DMSO was added dropwise to a suspension of 0.68 g of 95% pure NaH in 50 ml of dimethyl sulfoxide (DMSO). The mixture was stirred at 25–33° C. for 20 min, after which a solution of 4.4 g of methyl 2-(2-fluorophenyl)oxoacetate in 30 ml of DMSO was added dropwise. The reaction mixture was then stirred at 20–25° C. for 72 hours, poured into ice-water and extracted with methyl tert-butyl ether. The organic phases were washed with 1N aqueous sodium hydroxide solution and water and dried and then freed from the solvent. The residue was taken up in 1 liter of methanol and admixed with 143 ml of a 17.5% strength aqueous methoxyamine solution. The mixture was stirred at 20–25° C. for 12 hours, after which the methanol was distilled off, the residue was taken up in MtBE and water and the organic phases were dried. Removal of the solvent gave 4.0 g of the title compound as an E/Z-isomer mixture which was used without any further purification in Example 10.

Example 10

Preparation of Methyl E-[2-(4'-Chlorobiphenyl-3-yl-oxy)phenyl]methoxyiminoacetate

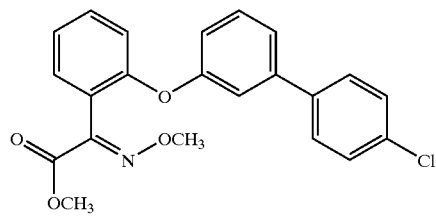

With ice-cooling, the solution of 2.5 g of the isomer mixture from Example 9 in 50 ml of methylene chloride was saturated with hydrogen chloride and stirred at 20–25° C. for 1 hour. Distillative removal of the solvent and silica gel chromatography (MtBE/cyclohexane=9:1) gave 1.5 g of pure E-isomer as a yellow oil.

$^1$H NMR (CDCl$_3$, ppm): δ=3.8 (3H); 4.0 (3H).

TABLE I

IB.1

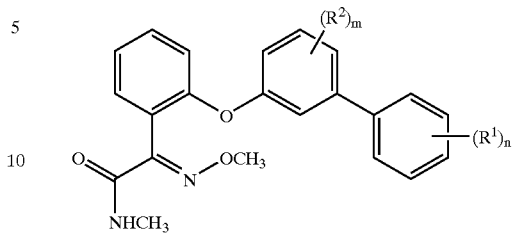

| No. | $(R^1)_n$ | $(R^2)_m$ | Phys. data (m.p. [° C.]; IR [cm$^{-1}$]; NMR [CDCl$_3$, ppm]) |
|---|---|---|---|
| I-1 | 4-Cl | H | 128–130 |
| I-2 | 4-CH$_3$ | H | 132–134 |
| I-3 | 4-isopropyl | H | 135–137 |
| I-4 | 3-F | H | 85–88 |
| I-5 | 4-Br | H | 56–59 |
| I-6 | 2,4-Cl$_2$ | H | 98–100 |
| I-7 | 4-CF$_3$ | H | 112–114 |
| I-8 | 2-F-4-CH$_3$ | H | 135–137 |
| I-9 | 4-COCH$_3$ | H | 137–139 |
| I-10 | 4-CHO | H | 57–60 |
| I-11 | 2-OCH$_3$ | H | 144–146 |
| I-12 | 4-tert.-butyl | H | 145–148 |
| I-13 | 4-F | H | 87–90 |
| I-14 | 3,5-Cl$_2$ | H | 149–152 |
| I-15 | 3,5-(CF$_3$)$_2$ | H | 1675, 1380, 1280, 1172, 1134 |
| I-16 | 4-[C(CH$_3$)=NOCH$_3$] | H | 48–51 |
| I-17 | 4-[CH=NOCH$_3$] | H | 1675, 1525, 1480, 1233, 1054, 1041 |
| I-18 | 3-Cl-4-F | H | 1674, 1478, 1237, 1040, 980 |
| I-19 | 2-CH$_3$ | H | 110–113 |
| I-20 | 3-CF$_3$ | H | 72–75 |
| I-21 | 2-OCH$_3$ | H | 135–137 |
| I-22 | 4-CH$_3$ | 4-F | 2.38; 2.9; 4.0; 6.8; 6.9–7.5 |
| I-23 | 4-F | 4-F | 2.9; 3.95; 6.8 |
| I-24 | 4-Cl | 4-F | 2.8; 4.0; 6.85 |

TABLE II

IB.2

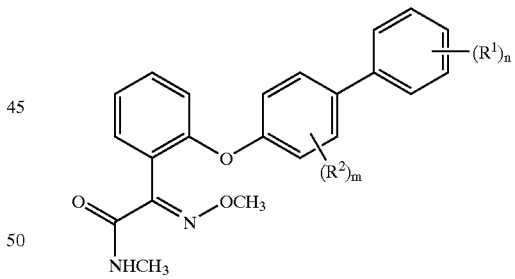

| No. | $(R^1)_n$ | $(R^2)_m$ | Phys. data (m.p. [° C.]; IR [cm$^{-1}$]; NMR [CDCl$_3$, ppm]) |
|---|---|---|---|
| II-1 | 4-F | H | 1668, 1242, 1032, 828 |
| II-2 | 2-F | H | 1665, 1241, 1038, 980 |
| II-3 | 2-Cl | H | 1673, 1240, 1037, 976 |
| II-4 | 3-Cl | H | 1671, 1241, 1038, 980, 786 |
| II-5 | 4-Cl | H | 1665, 1254, 1089, 1032, 823 |
| II-6 | 3-F | H | 1670, 1241, 1038, 980 |

Examples of the Activity Against Harmful Fungi

The fungicidal activity of the compounds of the formula I was demonstrated by the following experiments:

The active compounds were prepared separately or jointly as a 10% strength emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Wettol® EM (nonionic emulsifier based on ethoxylated castor oil) and diluted with water to the desired concentration.

Use Example 1

Activity Against Powdery Mildew of Wheat

Leaves of potted weed seedlings c.v. "Fruhgold" were sprayed to runoff point with an aqueous active compound preparation which had been prepared from a stock solution comprising 10% of active compound, 63% of cyclohexanone and 27% of emulsifier, and, 24 hours after the spray coating had dried on, dusted with spores of powdery mildew of wheat (Erysiphe graminis forma specialis tritici). The test plants were subsequently placed in a greenhouse at from 20 to 24° C. and a relative atmospheric humidity of from 60 to 90%. After 7 days, the extent of mildew development was determined visually as % infection of the total leaf area.

In this test, the plants which had been treated with 250 ppm of the active compounds I-1 to I-8 and I-10 to I-24 showed an infection of at most 5%, while the untreated plants showed an infection of 90%.

Use Example 2

Activity Against *Plasmopara viticola*

Leaves of potted grapevines cv. "Müller-Thurgau" were sprayed to runoff point with an aqueous active compound preparation which had been prepared using a stock solution comprising 10% of active compound, 63% of cyclohexanone and 27% of emulsifier. To assess the persistency of the substances, the plants were kept for 7 days in a greenhouse after the spray coating had dried on. Only then were the leaves inoculated with an aqueous zoospore suspension of *Plasmapara viticola*. The grapevines were then initially kept in a water vapor-saturated chamber at 24° C. for 48 hours and then in a greenhouse at 20–30° C. for 5 days. After this period of time, the plants were once more kept in a humid chamber for 16 hours to promote sporangiophore eruption. The extent of the infection on the undersides of the leaves was then determined visually.

In this test, the plants which had been treated with 16 ppm of the active compounds I-1, I-2, I-4 to I-11, I-13, I-16 and I-18 to I-24 showed an infection of at most 5%, while the untreated plants showed an infection of 90%.

We claim:

1. A 2-phenoxyphenylacetic acid compound of formula I:

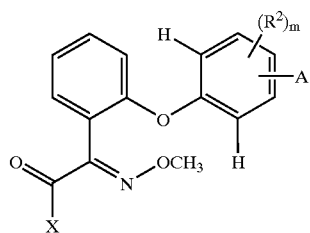

where the substituents and the index have the following meanings:

A is

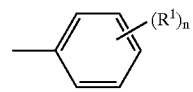

where $R^1$ is halogen, $C_1$–$C_4$-alkyl, $C_1$–$C_4$-alkoxy, $CF_3$, $C_1$–$C_4$-haloalkoxy, formyl, $C(=O)NR^aR^b$ or $C(R^a)=NOR^b$;

$R^a$ is hydrogen or $C_1$–$C_4$-alkyl;

$R^b$ is $C_1$–$C_4$-alkyl;

n is 1, 2, 3 or 4, where the groups $R^1$ are identical or different if n is not 1;

$R^2$ is halogen, $CH_3$ or $CF_3$;

m is 0 or 1; and

X is $OCH_3$ or $NHCH_3$.

2. A process for preparing the compound of formula I defined in claim 1, which comprises reacting a methyl α-phenyl-α-ketoacetate of formula II:

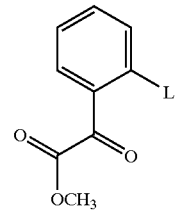

in which L is fluorine or chlorine under basic conditions with a phenol of formula III:

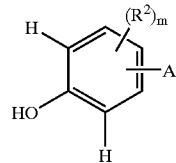

to give a methyl α-(2-phenoxyphenyl)-α-ketoacetate of formula IV:

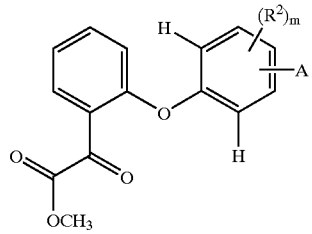

reacting IV with O-methylhydroxylamine or its acid addition salt to give an oxime ether of formula IA:

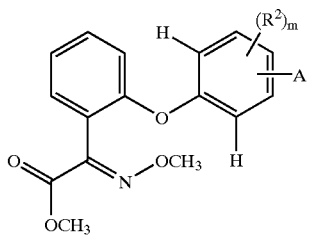

IA and, if X in formula I is NHCH$_3$, converting the ester group of the ether of formula IA with methylamine to give an amide of formula IB:

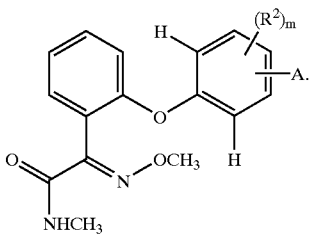

IB

3. The N-methyl-2-phenoxyphenylacetamide of formula I defined in claim 1, wherein X is NHCH$_3$.

4. The N-methyl-2-phenoxyphenylacetamide of formula I defined in claim 3, wherein A is bonded in 3-position relative to the ether oxygen.

5. The N-methyl-2-phenoxyphenylacetamide of formula I defined in claim 4 wherein m is 0.

6. A methyl α-(2-phenoxyphenyl)-α-ketoacetate of formula IV:

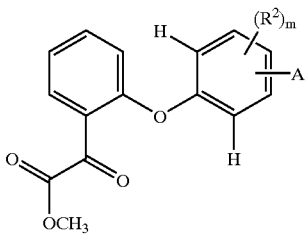

IV wherein
A is

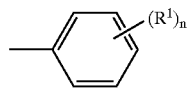

where
R$^1$ is halogen, C$_1$–C$_4$-alkyl, C$_1$–C$_4$-alkoxy, CF$_3$, C$_1$–C$_4$-haloalkoxy, formyl, C(=O)NR$^a$R$^b$ or C(R$^a$)=NOR$^b$;
R$^a$ is hydrogen or C$_1$–C$_4$-alkyl;
R$^b$ is C$_1$–C$_4$-alkyl;
n is 1, 2, 3 or 4, where the groups R$^1$ are identical or different if n is not 1;
R$^2$ is halogen, CH$_3$ or CF$_3$;
m is 0 or 1; and
X is OCH$_3$ or NHCH$_3$.

7. A composition suitable for controlling harmful fungi, comprising a solid or liquid carrier and the compound of formula I defined in claim 1.

8. A method of preparing the composition defined in claim 7 which comprises admixing the compound of formula I and at least one liquid or solid carrier.

9. A method for controlling harmful fungi, which comprises treating the fungi or materials, plants, soil or seeds to be protected against fungal attack with an effective amount of the compound of formula I defined in claim 1.

* * * * *